US008226554B2

(12) United States Patent
McBride et al.

(10) Patent No.: US 8,226,554 B2
(45) Date of Patent: Jul. 24, 2012

(54) RETRACTOR ASSEMBLIES FOR SURGERY IN A PATIENT

(75) Inventors: Larry McBride, Ripley, TN (US); Kelli N. Sebastian, Arlington, TN (US); Douglas D. Kave, Byhalia, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 766 days.

(21) Appl. No.: 12/262,100

(22) Filed: Oct. 30, 2008

(65) Prior Publication Data
US 2010/0113885 A1 May 6, 2010

(51) Int. Cl.
A61B 17/02 (2006.01)
(52) U.S. Cl. .......................... 600/219; 600/225; 600/201
(58) Field of Classification Search ................. 600/224, 600/219, 201, 213, 215, 222, 225, 228, 30
See application file for complete search history.

(56) References Cited

U.S. PATENT DOCUMENTS

| 563,236 | A | 6/1896 | Penhall |
| 1,400,616 | A | 12/1921 | McCrory |
| 1,613,141 | A | 1/1927 | Stain |
| 2,661,735 | A | 12/1953 | Darden |
| 2,670,731 | A | 3/1954 | Zoll et al. |
| 2,693,795 | A | 11/1954 | Grieshaber |
| 3,054,398 | A | 9/1962 | Kobler |
| 3,747,592 | A | 7/1973 | Santos |
| 3,752,149 | A | 8/1973 | Ungar et al. |
| 3,788,318 | A | 1/1974 | Kim et al. |
| 3,965,890 | A | 6/1976 | Gauthier |
| 4,156,424 | A * | 5/1979 | Burgin ........................ 600/213 |
| 4,263,899 | A | 4/1981 | Burgin |
| 4,380,999 | A | 4/1983 | Healy |
| 4,545,374 | A | 10/1985 | Jacobson |
| 4,716,901 | A | 1/1988 | Jackson et al. |
| 4,747,394 | A | 5/1988 | Watanabe |
| 4,765,311 | A | 8/1988 | Kulik et al. |
| 4,817,587 | A | 4/1989 | Janese |
| 4,852,552 | A | 8/1989 | Chaux |

(Continued)

FOREIGN PATENT DOCUMENTS
DE 8704901 U 7/1987
(Continued)

OTHER PUBLICATIONS
International Search Report and Written Opinion for US Application PCT/2009/062601 mailed on Jun. 8, 2010.

Primary Examiner — Kevin T Truong
Assistant Examiner — Zade Coley (57) ABSTRACT

An assembly for tissue retraction in surgery includes a pair of arm members removably positioned on and movable along an elongate support member. The arm members each include an external housing, a locking member positioned within the external housing and a passageway extending through the external housing and the locking member. The elongate support member extends through the passageways and the locking members are releasably biased into engagement with the elongate support member to allow the arm members to move in opposite directions along the elongate support member and prevent the arm members from moving toward one another. Each arm member further includes a rotatable engagement portion engageable with a respective retractor portion and a locking element releasably biased into engagement with the engagement portion to limit rotation of the engagement portion to a first direction relative to the arm member.

14 Claims, 6 Drawing Sheets

U.S. PATENT DOCUMENTS

| | | |
|---|---|---|
| 4,862,891 A | 9/1989 | Smith |
| 4,899,729 A | 2/1990 | Gill et al. |
| 5,027,793 A | 7/1991 | Engelhardt et al. |
| 5,052,373 A * | 10/1991 | Michelson .................... 600/217 |
| 5,088,472 A * | 2/1992 | Fakhrai ........................ 600/214 |
| 5,125,396 A | 6/1992 | Ray |
| 5,139,511 A | 8/1992 | Gill et al. |
| 5,158,545 A | 10/1992 | Trudell et al. |
| 5,163,949 A | 11/1992 | Bonutti |
| 5,197,971 A | 3/1993 | Bonutti |
| 5,299,563 A | 4/1994 | Seton |
| 5,312,417 A | 5/1994 | Wilk |
| 5,339,803 A | 8/1994 | Mayzels et al. |
| 5,353,784 A | 10/1994 | Nady-Mohamed |
| 5,389,080 A | 2/1995 | Yoon |
| 5,490,819 A | 2/1996 | Nicholas et al. |
| 5,503,617 A | 4/1996 | Jako |
| 5,509,893 A | 4/1996 | Pracas |
| 5,512,038 A | 4/1996 | O'Neal et al. |
| 5,549,595 A | 8/1996 | Freitas |
| 5,573,517 A | 11/1996 | Bonutti et al. |
| 5,618,260 A | 4/1997 | Caspar et al. |
| 5,667,481 A * | 9/1997 | Villalta et al. ................ 600/224 |
| 5,674,240 A | 10/1997 | Bonutti et al. |
| 5,681,265 A | 10/1997 | Maeda et al. |
| 5,688,223 A | 11/1997 | Rosendahl |
| 5,707,359 A | 1/1998 | Bufalini |
| 5,728,046 A | 3/1998 | Mayer et al. |
| 5,755,732 A | 5/1998 | Green et al. |
| 5,776,054 A | 7/1998 | Bobra |
| 5,779,629 A | 7/1998 | Hohlen |
| 5,785,648 A | 7/1998 | Min |
| 5,795,291 A * | 8/1998 | Koros et al. ................... 600/232 |
| 5,813,978 A | 9/1998 | Jako |
| 5,823,947 A | 10/1998 | Yoon et al. |
| 5,865,731 A | 2/1999 | Lenox et al. |
| 5,879,291 A | 3/1999 | Kolata et al. |
| 5,888,196 A | 3/1999 | Bonutti |
| 5,928,139 A | 7/1999 | Koros et al. |
| 5,931,777 A | 8/1999 | Sava |
| 5,931,778 A * | 8/1999 | Furnish ........................ 600/232 |
| 5,944,658 A | 8/1999 | Koros et al. |
| 5,951,466 A | 9/1999 | Segermark et al. |
| 5,961,499 A | 10/1999 | Bonutti |
| 5,967,972 A | 10/1999 | Santilli et al. |
| 5,976,146 A | 11/1999 | Ogawa et al. |
| 6,027,518 A | 2/2000 | Gaber |
| 6,042,540 A | 3/2000 | Johnston et al. |
| 6,074,343 A | 6/2000 | Nathanson et al. |
| 6,074,380 A | 6/2000 | Byrne et al. |
| 6,083,154 A | 7/2000 | Liu et al. |
| 6,096,046 A | 8/2000 | Weiss et al. |
| 6,099,547 A | 8/2000 | Gellman et al. |
| 6,132,370 A | 10/2000 | Furnish et al. |
| 6,139,493 A | 10/2000 | Koros et al. |
| 6,149,583 A | 11/2000 | Vierra et al. |
| 6,162,236 A | 12/2000 | Osada |
| 6,171,299 B1 | 1/2001 | Bonutti |
| 6,187,000 B1 | 2/2001 | Davison et al. |
| 6,196,969 B1 | 3/2001 | Bester et al. |
| 6,200,322 B1 | 3/2001 | Branch et al. |
| 6,224,545 B1 | 5/2001 | Cocchia et al. |
| 6,296,609 B1 | 10/2001 | Brau |
| 6,312,443 B1 | 11/2001 | Stone |
| 6,325,812 B1 | 12/2001 | Dubrul et al. |
| 6,361,492 B1 | 3/2002 | Santilli |
| 6,371,911 B1 | 4/2002 | Hossain et al. |
| 6,394,950 B1 | 5/2002 | Weiss |
| 6,431,025 B1 | 8/2002 | Koros et al. |
| 6,450,952 B1 | 9/2002 | Rioux et al. |
| 6,602,189 B1 | 8/2003 | Bennetti et al. |
| 6,616,605 B2 | 9/2003 | Wright |
| 6,749,563 B2 | 6/2004 | Stihl |
| 6,945,933 B2 | 9/2005 | Branch et al. |
| 7,147,599 B2 * | 12/2006 | Phillips et al. ................. 600/232 |
| 7,252,673 B2 * | 8/2007 | Lim ............................... 606/99 |
| 7,537,565 B2 * | 5/2009 | Bass ............................ 600/219 |
| 7,654,954 B1 * | 2/2010 | Phillips et al. ................. 600/228 |
| 7,824,332 B2 * | 11/2010 | Fakhrai ........................ 600/232 |
| 7,922,658 B2 * | 4/2011 | Cohen et al. .................. 600/223 |
| 2003/0055319 A1 | 3/2003 | Chang |
| 2004/0002629 A1 | 1/2004 | Branch et al. |
| 2004/0049101 A1 * | 3/2004 | Phillips et al. ................. 600/219 |
| 2004/0176665 A1 | 9/2004 | Branch et al. |
| 2004/0230191 A1 | 11/2004 | Frey et al. |
| 2005/0113644 A1 | 5/2005 | Obenchain et al. |
| 2005/0159651 A1 * | 7/2005 | Raymond et al. ............. 600/213 |
| 2005/0192485 A1 | 9/2005 | Branch et al. |
| 2005/0234304 A1 | 10/2005 | Dewey et al. |
| 2006/0069315 A1 | 3/2006 | Miles et al. |
| 2006/0217806 A1 * | 9/2006 | Peterman et al. ........... 623/17.11 |
| 2008/0177270 A1 * | 7/2008 | Sorrenti et al. ................. 606/90 |
| 2009/0036746 A1 * | 2/2009 | Blackwell et al. ............ 600/219 |
| 2009/0076516 A1 * | 3/2009 | Lowry et al. .................... 606/90 |
| 2009/0306480 A1 * | 12/2009 | Protopsaltis ................... 600/219 |
| 2010/0081885 A1 * | 4/2010 | Wing et al. .................... 600/215 |

FOREIGN PATENT DOCUMENTS

| | | |
|---|---|---|
| EP | 0856286 | 8/1998 |
| EP | 0951868 | 10/1999 |
| EP | 1053717 A | 11/2000 |
| EP | 1192905 | 9/2001 |
| FR | 1019217 | 10/1952 |
| FR | 2788958 | 8/2000 |
| FR | 2807313 | 10/2007 |
| WO | 9915081 A1 | 4/1999 |
| WO | 2005030318 | 4/2005 |

* cited by examiner

RETRACTOR ASSEMBLIES FOR SURGERY IN A PATIENT

BACKGROUND

The present application relates to retractor assemblies and methods for use in performing surgery in a patient, and more particularly, but not exclusively, relates to assemblies for tissue retraction to facilitate a procedure within a patient through the retracted tissue.

Traditional surgical procedures for pathologies located within the body can cause significant trauma to the intervening tissues. These procedures often require a long incision, extensive muscle stripping, prolonged retraction of tissues, denervation and devascularization of tissue. These procedures can require operating room time of several hours and several weeks of post-operative recovery time due to the destruction of tissue during the surgical procedure. In some cases, these invasive procedures lead to permanent scarring and pain that can be more severe than the pain leading to the surgical intervention.

The development of surgical procedures has yielded a major improvement in reducing recovery time and post-operative pain because minimal dissection of tissue, such as muscle tissue, is required. For example, minimally invasive surgical techniques are desirable for spinal and neurosurgical applications because of the need for access to locations within the body and the danger of damage to vital intervening tissues. While developments in surgical procedures have provided steps in the right direction, there remains a need for further development in tissue retraction devices and methods.

SUMMARY

One nonlimiting embodiment of the present application is directed to an assembly for surgery in a patient that includes a pair of arm members removably positioned on and movable along an elongate support member. The arm members each include an external housing, a locking member positioned within the external housing and a passageway extending through the external housing and the locking member. The elongate support member extends through the passageways and the locking members are releasably biased into engagement with the elongate support member to allow the arm members to move in opposite directions along the elongate support member and prevent the arm members from moving toward one another.

In a further form of this embodiment, each arm member also includes a rotatable engagement portion engageable with a respective retractor portion and a locking element releasably biased into engagement with the engagement portion. The engagement between the locking elements and the engagement portion limits rotation of the engagement portions to a single direction about a longitudinal axis of a respective arm member.

However, in other embodiments, different forms and applications are envisioned.

Another embodiment of the present application is a unique system for surgery in a patient. Other embodiments include unique methods, systems, devices, kits, assemblies, equipment, and/or apparatus involving a retractor.

Further embodiments, forms, features, aspects, benefits, objects and advantages of the present application shall become apparent from the detailed description and figures provided herewith.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

Instruments, assemblies and methods for performing surgery, including spinal surgeries that include one or more techniques such as laminotomy, laminectomy, foraminotomy, facetectomy, discectomy, interbody fusion, spinal nucleus or disc replacement, and implant insertion including plates, rods, and bone engaging fasteners, for example, are provided. The surgery is performed through a working channel or passageway through skin and/or tissue of the patient provided by a retractor assembly which includes a retractor. Viewing of the surgical site at the working end of the retractor can be accomplished with naked eye visualization, microscopic viewing devices, loupes, viewing instruments mounted on the retractor, positioned over the retractor, positioned in other portals in the body, and/or through a viewing system such as lateral fluoroscopy. The retractor is movable in situ to increase the size of the working channel to facilitate access to the working space at the distal end of the retractor while minimizing trauma to tissue surrounding the retractor. The retractor can be used with any surgical approach to the spine, including anterior, posterior, posterior mid-line, lateral, postero-lateral, and/or antero-lateral approaches, and in other regions besides the spine.

Figure 1:
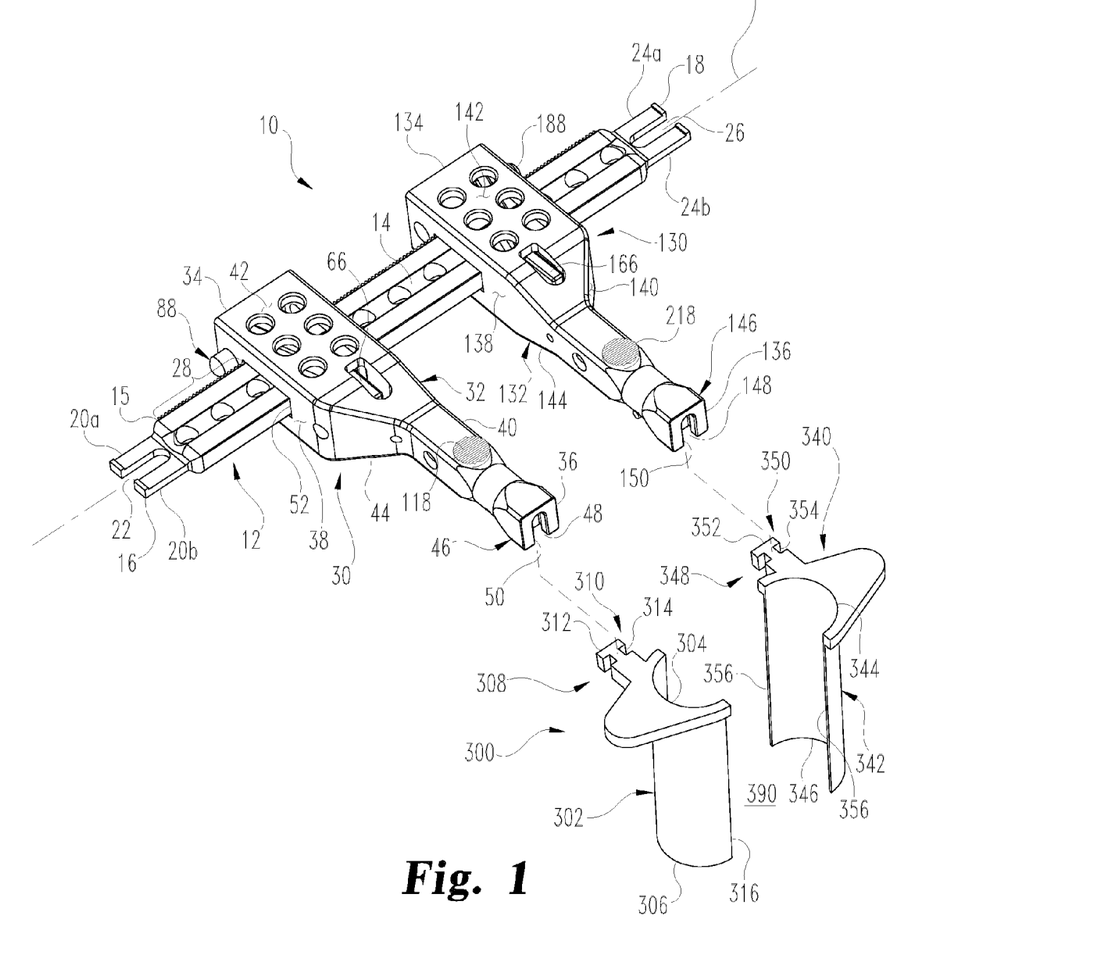
FIG. 1 is perspective view of an assembly for tissue retraction surgery in a patient.
Figure 2:
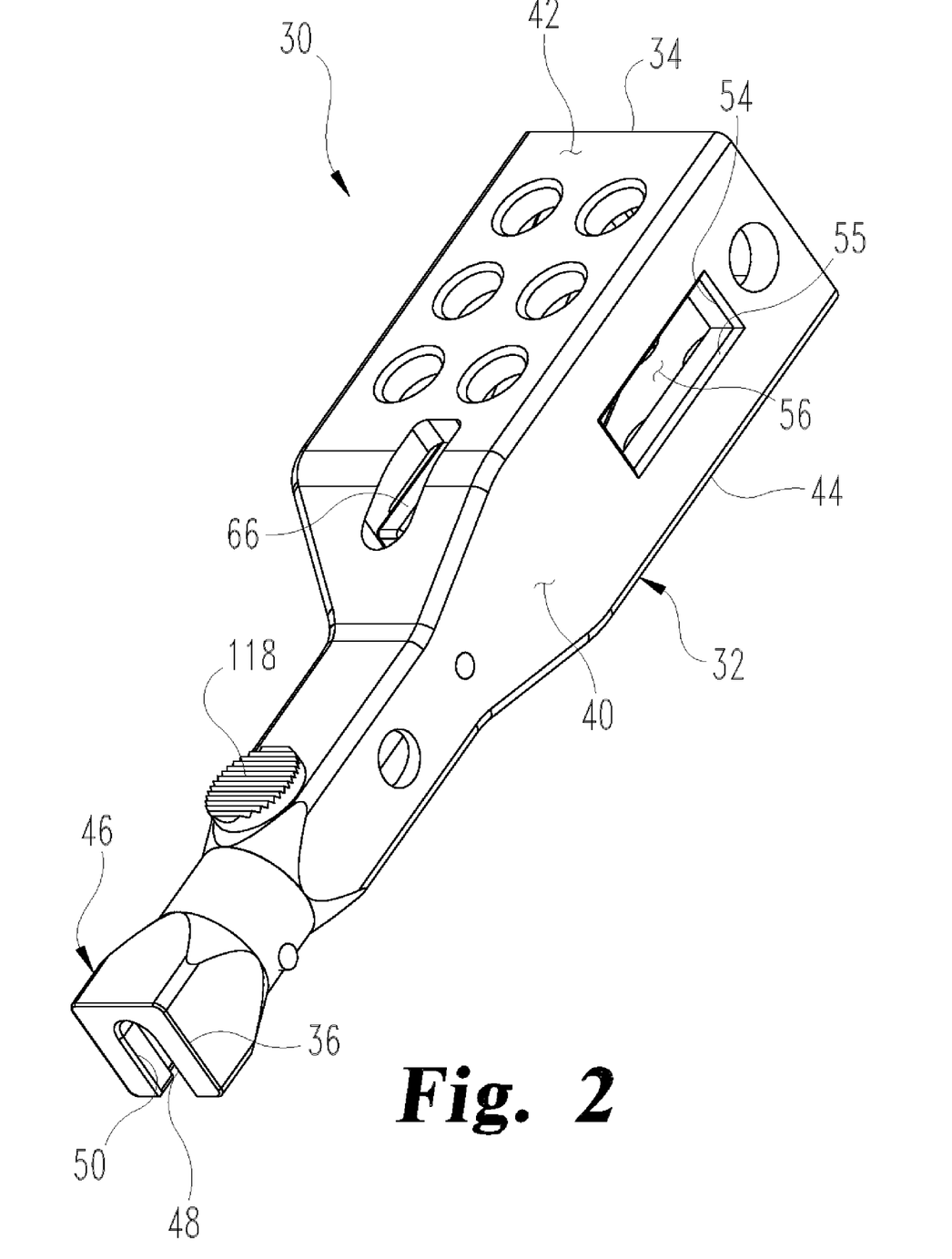
FIG. 2 is a perspective view of one arm member of the assembly of FIG. 1.

Referring now generally to FIG. 1, there is illustrated in perspective view one embodiment retractor assembly 10. Assembly 10 includes an elongate support member 12 including an elongate body 14 extending along a longitudinal axis L between a first end 16 and an opposite second end 18. First end 16 and second end 18 are generally structured to engage with one or more operating room support structures. More particularly, first end 16 includes a pair of oppositely positioned flange members 20a and 20b which define a slot 22 positioned therebetween. Similarly, second end 18 includes a pair of oppositely positioned flange members 24a and 24b which define a slot 26 positioned therebetween. In one form, it is contemplated that slots 22, 26 can be configured to receive a corresponding fastening member from the operating room support structure. Examples of operating room support structures include, without limitation, support arms, braces and other linkage members which are coupled to an operating table or bed and movable to position assembly 10 relative to a surgical site of the patient. Elongate support member 12 also includes a plurality of teeth 28 positioned on proximal surface 15 thereof. In other non-illustrated embodiments, other surface features such as serrations, knurling, notches, grooves, indentations, projections and/or polymeric, ceramic or metallic coatings, could be provided on proximal surface 15 of elongate support member 12 in addition to or in lieu of teeth 28, as well as on one or more additional surfaces of elongate support member 12. Still, in other embodiments, it is contemplated that elongate support member 12 is free from any surface features.

Assembly 10 also includes a first arm member 30 and a second arm member 130. First and second arm members 30, 130 are removably positioned on and movable along elongate support member 12, further details of which will be provided below. First arm member 30 includes an external housing 32 that extends between a proximal end 34 and a distal end 36. External housing 32 also includes a pair of lateral sidewalls 38, 40 which extend between an upper surface 42 and a lower surface 44. Distal end 36 includes an engagement portion 46 which is structured to engage with first retractor portion 300. Similarly, second arm member 130 includes an external housing 132 that extends between a proximal end 134 and a distal end 136. External housing 132 also includes a pair of lateral sidewalls 138, 140 which extend between an upper surface 142 and a lower surface 144. Distal end 136 includes an engagement portion 146 which is structured to engage with second retractor portion 340. First and second arm members 30, 130 are generally operable to move relative to each other to provide a working channel 390 to a surgical site between first retractor portion 300 and second retractor portion 340. Further details regarding operation of assembly 10 are provided below.

Retractor portion 300 includes a retractor blade 302 extending between a first end 304 and an opposite second end 306. Retractor portion 300 also includes an engagement assembly 308 positioned at first end 304 of retractor blade 302. Engagement assembly 308 is structured to engage with engagement portion 46 of first arm member 30 and includes an extension 310 extending laterally from first end 304. In the illustrated embodiment, extension 310 extends substantially transversely to and in the same plane as first end 304 of retractor blade 302. However, in other non-illustrated embodiments, it is contemplated that extension 310 could be angled relative to first end 304 and/or could be positioned in a separate plane from first end 304. Extension 310 is defined by an enlarged portion 312 and a reduced profile stem portion 314. Retractor portion 340 includes a retractor blade 342 extending between a first end 344 and an opposite second end 346. Retractor portion 340 also includes an engagement assembly 348 positioned at first end 344 of retractor blade 342. Engagement assembly 348 is structured to engage with engagement portion 146 of second arm member 130 and includes an extension 350 extending laterally from first end 344. In the illustrated embodiment, extension 350 extends substantially transversely to and in the same plane as first end 344 of retractor blade 342. However, in other non-illustrated embodiments, it is contemplated that extension 350 could be angled relative to first end 344 and/or could be positioned in a separate plane from first end 344. Extension 350 is defined by an enlarged portion 352 and a reduced profile stem portion 354.

Engagement portions 46 and 146 each includes a respective recess 48, 148 which opens to receive a respective engagement assembly 308, 348 of first and second retractor portions 300, 340. Recess 48 includes a keyway opening 50 and a receptacle (not shown) in communication with opening 50. The receptacle is enlarged relative to opening 50, and is shaped to receive enlarged portion 312 of engagement assembly 308 of retractor portion 300 therein. Similarly, recess 148 includes a keyway opening 150 and a receptacle (not shown) in communication with opening 150. The receptacle is enlarged relative to opening 150, and is shaped to receive enlarged portion 352 of engagement assembly 348 of retractor portion 340 therein. Openings 50, 150 and the receptacles in communication therewith are open along the bottom surface 44, 144 of the respective engagement portions 46, 146 to facilitate placement of enlarged portions 312, 352 of engagement assemblies 308, 348 therein. When enlarged portions 312, 352 are positioned in the respective receptacle of engagement portions 46, 146, stems 314, 354 of engagement assemblies 308, 348 extend through openings 50, 150.

Figure 3:
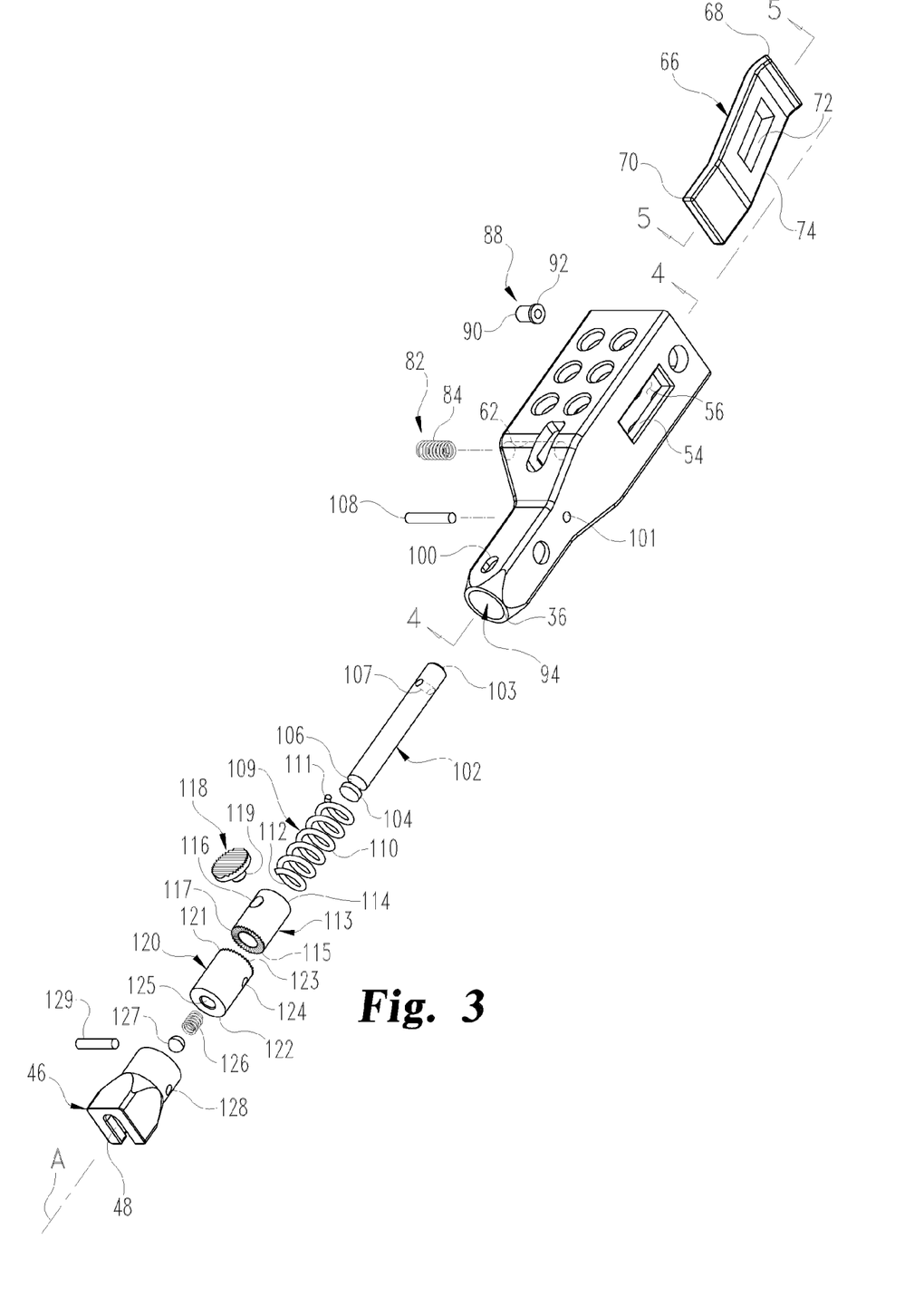
FIG. 3 is a perspective, exploded assembly view of the arm member of FIG. 2.
Figure 4:
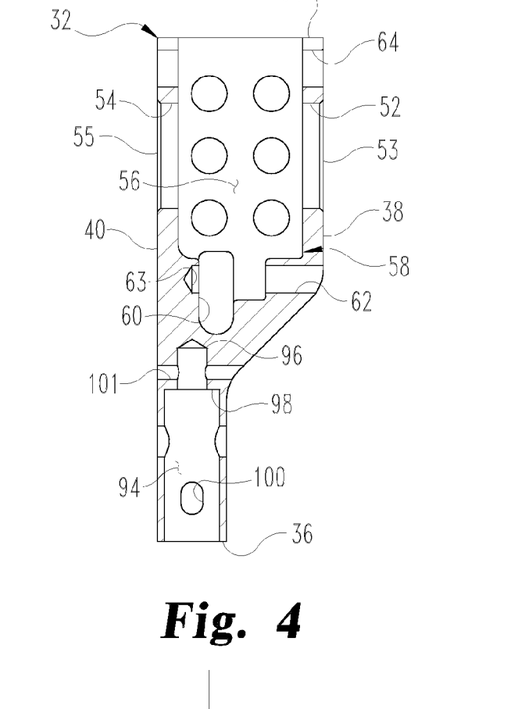
FIG. 4 is a section view of the external housing of the arm member of FIG. 3.

In one or more forms, it is contemplated that engagement portions 46, 146 can include a locking or clamping mechanism structured to releasably hold engagement assemblies 308, 348 in engagement therewith. For example, in one configuration as illustrated in FIG. 3 with respect to first arm member 30, a ball detent mechanism is utilized. More particularly, a ball member 127 is biased distally by a spring member 126 and protrudes into the receptacle of engagement portion 46. Ball member 127 can be depressed proximally from the receptacle of engagement portion 46 when enlarged portion 312 of engagement assembly 308 is being positioned therein, and then return to its distally biased position and be received within an indentation (not shown) on enlarged portion 312 once engagement assembly 308 is positioned in the receptacle of engagement portion 46. Ball member 127 can be similarly depressed to facilitate removal of retractor portion 300 from engagement portion 46 by a user. While the ball detent mechanism has been described with respect to first arm member 30 and retractor portion 300, it should be appreciated that this arrangement and the description thereof are also applicable to the engagement between first arm member 130 and retractor portion 340.

Other arrangements are also contemplated for releasably securing the engagement between first and second arm members 30, 130 and respective retractor portions 300, 340. Examples of such arrangements include dovetail connections, fasteners, threaded coupling members, clamping members, snap rings, compression bands, straps and releasably interlocking cams or tabs, just to name a few possibilities. Other configurations for recesses 48, 148 are also contemplated, including recesses that are enclosed, uniform, or any other suitable configuration to receive at least a portion of a respective engagement assembly 308, 348. Still other embodiments contemplate that engagement portions 46, 146 do not include recesses, but rather are shaped for receipt in or otherwise engage the respective engagement assembly 308, 348 of retractor portions 300, 340. In yet another embodiment, it is contemplated that engagement portions 46, 146 and engagement assemblies 308, 348 of retractor portions 300, 340 are integrally formed.

With further respect to retractor portions 300, 340, ends 306, 346 can be beveled to facilitate insertion in an incision, although non-beveled ends are also contemplated. Retractor blade 302 can be positioned adjacent to or mated with retractor blade 342 along adjacent ones of the longitudinal edges 316 of retractor blade 302 and longitudinal edges 356 of retractor blade 342. A working channel 390 is formed between first retractor blade 302 and second retractor blade 342 and extends between and opens at first ends 304, 344 and second ends 306, 346. In one non-illustrated form, retractor portion 300, 340 may be provided with engagement members structured to engage with one or more surgical instruments, such as a separation instrument, which are used with assembly 10. In other non-illustrated embodiments, it is contemplated that one or both of arm members 30, 130 can include an engagement member in addition to or in lieu of the engagement members on retractor portions 300, 340.

Retractor blades 302, 342 are insertable through an incision in skin and tissue of a patient to provide working channel 390 to a surgical site. It is contemplated that retractor blades 302, 342 are inserted through skin and tissue in an insertion configuration for working channel 390. In the insertion configuration, working channel 390 is substantially enclosed or circumscribed by retractor blades 302, 342. After insertion into the patient, working channel 390 can be enlarged by separating first retractor blade 302 and second retractor blade 342. Separation of retractor blades 302, 342 increases the size of working channel 390 from first ends 304, 344 to second ends 306, 346.

Working channel 390 can have a size in the insertion configuration that allows passage of one or more surgical instruments and/or implants to the surgical location in the patient's body. It may be desirable during surgery to provide greater access to the surgical site in the patient's body beyond the locations provided through working channel 390 in its insertion configuration. First retractor blade 302 and second retractor blade 342 are movable away from one another to enlarge working channel 390. In the enlarged configuration of working channel 390, a space is formed between the adjacent longitudinal edges 316, 356 of retractor blades 302, 342. The space between the adjacent longitudinal edges 316, 356 exposes enlarged working channel 390 to skin and tissue of the patient between the separated first retractor blade 302 and second retractor blade 342. This exposed tissue can also be accessed by the surgeon through the enlarged working channel 390 with one or more instruments and/or implants. It is further contemplated that a shield, guard or tissue retractor could be placed in enlarged working channel 390 to maintain the exposed tissue away from the enlarged working channel 390. Various non-limiting examples of additional tissue retractors that can be positioned in the enlarged working channel 390 between retractor blades 302, 342 are provided in U.S. Patent Publication No. 2004/0176665 to Branch et al., the contents of which are incorporated herein by reference in their entirety.

Viewing instruments can be positioned in or adjacent to working channel 390 to facilitate surgeon viewing of the surgical site. For example, an endoscopic viewing element can be mounted on the first end of one of retractor blades 302, 342 with a scope portion extending along working channel 390. A microscopic viewing element can be positioned over the first end of one of retractor blades 302, 342 for viewing the surgical site. Other imaging techniques, such as lateral fluoroscopy, can be used alone or in combination with the endoscopic and microscopic viewing elements. It is further contemplated that other instruments can be mounted on the first end of one or both of retractor blades 302, 342, such as nerve root retractors, tissue retractors, forceps, cutter, drills, scrapers, reamers, separators, rongeurs, taps, cauterization instruments, irrigation and/or aspiration instruments, illumination instruments, inserter instruments, and the like for use in surgical procedures at the surgical site. Such viewing instruments and other instruments can be employed with working channel 390 in its initial insertion configuration and/or its enlarged configuration.

In one non-illustrated form, retractor blades 302, 342 may be structured to align and releasably couple with one another in the insertion configuration. For example, retractor blade 302 can include an alignment pin structured to engage with a corresponding alignment aperture on retractor blade 342. Similarly, retractor blade 342 may include an alignment pin structured to engage with a corresponding alignment aperture on retractor blade 302. Other arrangements are also contemplated for aligning and releasably coupling first retractor blade 302 and second retractor blade 342 to one another. Examples of such arrangements include dovetail connections, fasteners, threaded coupling members, clamping members, snap rings, compression bands, straps, ball-detent mechanisms, and releasably interlocking cams or tabs, just to name a few possibilities.

First retractor blade 302 has a perimeter length along second end 306 which can be about the same as the perimeter length of retractor blade 302 at first end 304. Second retractor blade 342 includes a perimeter length along second end 346 which can be about the same as the perimeter length of retractor blade 342 adjacent first end 344. Retractor blades 302, 342 can have a semi-circular cross-section, and form a generally circular cross-section for the working channel when placed adjacent one another. Other cross-sectional shapes are also contemplated for first and second retractor blades 302, 342, such as, for example, any open sided polygonal shape, curved shape, or combined curved/polygonal shape. When retractor blades 302, 342 are separated from one another, working channel 390 can have a cylindrical or frusto-conical shape with, for example, a cross-section that is oval, elliptical, circular, curved, polygonal, or combined polygonal/curved in shape.

Retractor blades 302, 342 can be provided with sufficient rigidity between their first and second ends to separate and maintain separation of tissue when blades 302, 342 are initially inserted and also when the tissue is retracted by moving first retractor blade 302 and second retractor blade 342 away from one another. For example, retractor blades 302, 342 can include a thickness which provides sufficient rigidity to resist bending or bowing under the forces exerted on it by the retracted tissue. Also, the semicircular shaped cross-section of blades 302, 342 can be configured to provide a sufficient section modulus or moment of inertia in the direction of movement of blades 302, 342 to resist bending, bowing and/or deflection forces applied during such movement.

One particular application for retractor assembly 10 is in spinal surgery. It is contemplated that, after insertion of retractor blades 302, 342, they are separated predominantly in one direction to retract muscle and tissue which extends between first and second retractor portions 300, 340. For example, first and second retractor blades 302, 342 can be primarily or predominantly separable in the direction of the spinal column axis. The muscle tissue adjacent the spine has a fiber orientation that extends generally in the direction of the spinal column axis. The separation of retractor blades 302, 342 can also separate the muscle tissue along the fibers, thus the amount of separation and the resultant tearing and trauma to the muscle tissue can be minimized. It is also contemplated in other techniques employing retractor assembly 10 that working channel 390 can be enlarged primarily in a direction other than along the spinal column axis or in areas other than spine.

In one example, a method for positioning retractor blades 302, 342 through the skin and tissue includes making an incision through skin adjacent the location of a surgical site. For example, in spinal surgery, the incision can be made at a vertebral level at a location that provides access to the disc space between adjacent vertebrae or to one or more vertebra through a desired approach. Prior to insertion of retractor blades 302, 342, the skin and tissue can be sequentially dilated via a dilation instrument set (not illustrated) which can include guidewires and/or one or more tissue dilators of increasing size. The tissue dilators are inserted one over another to form a pathway through the skin and tissue to the surgical site in the patient. In such procedures, retractor blades 302, 342 are positioned over the last inserted dilator to form the pathway in the skin and tissue. Working channel 390 through retractor blades 302, 342 provides access to the surgical site at the second ends 306, 346 of retractor blades 302, 342 when the guidewires and dilators, if used, are removed therefrom.

For the entire surgery or for certain procedures during the surgery, it may be desired by the surgeon to increase the size of working channel 390 to facilitate access to the surgical site. First and second retractor blades 302, 342 of assembly 10 can be separated from their insertion configuration to a separated configuration in which working channel 390 is enlarged. In the enlarged configuration, first retractor blade 302 and second retractor blade 342 can be moved laterally away from one another by arm members 30, 130, further details of which are provided below. Adjacent ones of the edges 316, 356 are separated and working channel 390 is exposed to skin and tissue while first and second retractor blades 302, 342 hold tissue out of the operative field.

As indicated above, first and second arm members 30, 130 can be moved along elongate support member 12 to adjust the spacing between first and second retractor portions 300, 340. Referring generally to FIGS. 1-6, further details regarding the engagement between first arm member 30 and elongate support member 12, as well as additional features of first arm member 30, will be described. It should be appreciated that, unless otherwise indicated, second arm member 130 includes elements and features corresponding to those described with respect to first arm member 30, and the description regarding same is equally applicable to second arm member 130. Moreover, like numbers will be used to describe like features of first arm member 30 and second arm member 130. Additionally, while not illustrated, it should be appreciated that assembly 10 could be provided with first arm member 30 and optionally include an alternatively configured arm member in lieu of second arm member 130. For example, among other possibilities, arm member 130 could be replaced with an arm member that is fixed relative to elongate support member 12.

First arm member 30 includes a first passage 52 extending through lateral sidewall 38 (as shown in FIG. 1) and a second passage 54 extending through lateral sidewall 40. Passages 52, 54 communicate with an internal chamber 56 defined by external housing 32 and are each enclosed by a portion of the respective lateral sidewall 38, 40 extending continuously therearound. Additionally, passages 52, 54 generally correspond in size and shape to the external profile of elongate support member 12, and are in substantial axial alignment with each other to facilitate positioning of elongate support member 12 through passages 52, 54, external housing 32 and internal chamber 56, as illustrated in FIG. 1. More particularly, passages 52, 54 have a generally rectangular configuration which corresponds to the size and shape of the cross-sectional profile of elongate support member 12 along longitudinal axis L, although it is contemplated that passages 52, 54 could be configured differently in alternative embodiments. Chamfer 53, 55 is provided between passages 52, 54 and lateral sidewalls 38, 40 to facilitate engagement with and movement along elongate support member 12 of first arm member 30, although embodiments excluding such feature are contemplated.

Figure 5:
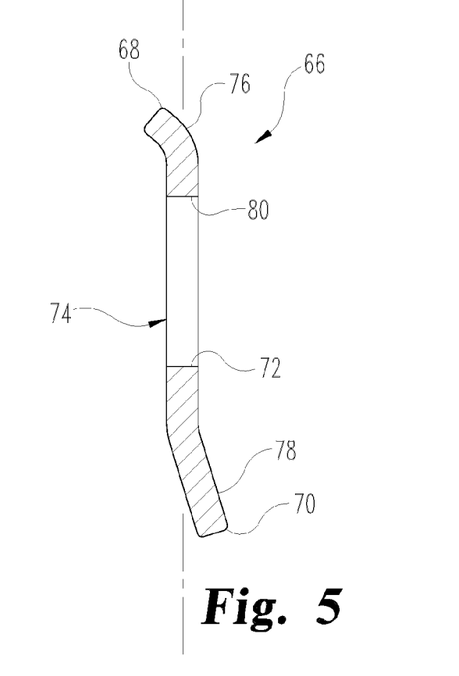
FIG. 5 is a section view of the locking member illustrated in FIG. 3.

Internal chamber 56 is generally sized and shaped to house a locking member 66. Locking member 66 includes an intermediate portion 74 positioned between a proximal end portion 68 and a distal end portion 70. As illustrated in FIG. 5 for example, proximal end portion 68 and distal end portion 70 are angled relative to intermediate portion 74 such that proximal end portion 68 extends in a first direction from intermediate portion 74 and is laterally offset from distal end portion 70 which extends in a second direction from intermediate portion 74. Proximal end portion 68 and distal end portion 70 each includes a flat portion 76, 78, respectively, with flat portion 78 being larger than flat portion 76. Intermediate portion 74 includes an opening 72 extending through locking member 66. When locking member 66 is positioned in internal chamber 56, opening 72 is generally aligned with passages 52, 54 to define a passageway through which elongate support member 12 can be positioned, as illustrated in FIG. 1 for example. With further reference to FIG. 5 for example, opening 72 is continuously enclosed by the surrounding portions of intermediate portion 74. In this configuration, opening 72 circumscribes elongate support member 12 when it is positioned in the passageway defined by opening 72 and passages 52, 54. As also illustrated in FIG. 5 for example, opening 72 includes a leading edge 80 which is engageable with proximal surface 15 of elongate support member 12 when it is positioned through opening 72, further details of which will be provided below.

Internal chamber 56 extends from proximal end 34 of external housing 32 to a distal portion 58. While not illustrated, it should be appreciated that a cover can be provided to enclose internal chamber 56 at proximal end 34. Distal portion 58 includes a receptacle 60 positioned between lateral sidewalls 38, 40 and sized and structured to receive distal end portion 70 of locking member 66. When positioned in receptacle 60, distal end portion 70 is generally restrained from lateral movement in internal chamber 56. A transverse bore 62 extends through lateral sidewall 38 into communication with receptacle 60 and terminates at end wall 63. As illustrated in the assembly view of FIG. 3, a compressible biasing member 82 in the form of coil spring 84 is positioned in transverse bore 62 and is compressed between locking member 66 and external housing 32. More particularly, a first end of spring 84 engages with end wall 63 of bore 62 and a second end of spring 84 engages with flat portion 78 of distal end portion 70 of locking member 66. In other non-illustrated forms, biasing member 82 may be alternatively configured such as, for example, a leaf spring, a split washer or a compressible polymer of elastic member, just to name a few possibilities.

When spring 84 is compressed between end wall 63 and locking member 66, distal end portion 70 and proximal end portion 68 of locking member 66 are biased toward lateral sidewall 38. In this arrangement, leading edge 80 of opening 72 engages with proximal surface 15 of elongate support member 12 to limit movement of first arm member 30 along elongate support member 12, further details of which will be provided below with respect to FIGS. 8-9. First arm member 30 also includes a release button 88 that includes a user engagement portion 90 and an enlarged flange 92. Release button 88 is positionable in bore 64 which extends through lateral sidewall 38 into communication with internal chamber 56. More particularly, user engagement portion 90 can extend through bore 64 with enlarged flange 92 positioned against the interior surface of lateral sidewall 38. Enlarged flange portion 92 is also engageable with flat portion 76 of proximal end portion 68 of locking member 66. In this configuration, release button 88 can be depressed by a user into engagement with locking member 66, moving proximal end portion 68 toward lateral sidewall 40. As a result, leading edge 80 of opening 72 becomes disengaged from proximal side 15 of elongate support member 12 and first arm member 30 is freely movable along elongate support member 12. In one form, a biasing mechanism can be utilized that positions release button 88 in an extended configuration (illustrated in FIG. 1 for example) when not being engaged by a user. In another form, it is contemplated that release button 88 could be interconnected with locking member 66, utilizing for example, a threaded interconnection. Still, in yet another form it is contemplated that release button 88 could be integrally formed with locking member 66.

Other configurations are contemplated for biasing locking member 66 into engagement with elongate support member 12. For example, in one non-illustrated form, biasing member 82 is replaced by a biasing member positioned in internal chamber 56 between proximal end portion 68 of locking member 66 and lateral sidewall 40. In this configuration, the biasing member directly applies a biasing force against proximal end portion 68 and forces proximal end portion 68 toward lateral sidewall 38. Similar to the illustrated embodiment described above, the biasing member can be compressed when release button 88 is depressed by a user to facilitate disengagement of locking member 66 from proximal surface 15 of elongate support member 12 so that first arm member 30 can be freely moved along elongate support member 12.

External housing 32 also defines an elongated, internal receptacle 94 extending from distal end 36 to a proximal end portion 96. Proximal end portion 96 is positioned distally of distal portion 58 of internal chamber 56 and is reduced in size relative to the remainder of receptacle 94, thereby providing an enlarged shoulder portion 98 in receptacle 94 adjacent to proximal end portion 96. First arm member 30 further includes an elongated pin 102 having a cylindrical body extending between a proximal end 103 positionable in proximal end portion 96 and an opposite distal end 104. Elongated pin 102 includes transverse bore 107 adjacent to proximal end 103. When distal end 103 of elongated pin 102 is positioned in proximal end portion 96, transverse bore 107 is aligned with bore 101 which extends through lateral sidewalls 38, 40 of external housing 32. In this arrangement, a cross pin 108 can be inserted through bores 101, 107 to couple elongated pin 102 with first arm member 30.

First arm member 30 also includes a compressible biasing member 109 in the form of coil spring 110 and a first spline member 113, each of which includes an axial bore and is positionable over elongated pin 102 in receptacle 94. In other non-illustrated forms, biasing member 109 may be alternatively configured such as, for example, a leaf spring, a split washer or a compressible polymer of elastic member, just to name a few possibilities. Further details of biasing member 109 and first spline member 113 will be provided below. A second spline member 120 is also provided and includes an axial bore structured to receive and engage with distal end 104 of pin elongated 102. Second spline member 120 is also engageable with a proximal internal receptacle (not shown) of engagement portion 46. More particularly, elongated pin 102 includes an annular groove 106 adjacent to distal end 104 which aligns with bore 124 of spline member 120 when elongated pin 102 is positioned in the axial bore thereof. Further, when spline member 120 is positioned in the proximal internal receptacle of engagement portion 46, annular groove 106, bore 124 and bore 128, which extends through engagement portion 46, are all aligned. A cross pin 129 can be inserted through bores 124, 128 and across annular groove 106 to couple engagement portion 46, spline member 120 and elongated pin 102. It should appreciated that bores 124, 128 are offset from the center of engagement portion 46 and spline member 120, respectively, to allow cross pin 108 to extend across annular groove 106. In this arrangement, engagement portion 46 is free to rotate about distal end 104 of elongated pin 102.

While not previously described, it should be appreciated that ball member 127 and spring 126 should be assembled with engagement portion 46 before engagement portion 46, spline member 120 and elongated pin 102 are coupled together. More particularly, ball member 127 is positioned in an opening (not shown) between the proximal internal receptacle of engagement portion 46 and recess 48. The opening should be appropriately sized to allow a portion of ball member 127 to protrude into recess 48 while preventing ball member 127 from entirely passing into recess 48 from the proximal internal receptacle. Once ball member 127 is appropriately positioned, one end of spring 126 is positioned into engagement therewith. The other end of spring 126 extends through an opening 125 in distal end 122 of spline member 120 and engages with distal end 104 of elongated pin 102 when engagement portion 46, spline member 120 and elongated pin 102 are coupled together. The engagement between spring 126 and elongated pin 102 compresses spring 126 and distally biases ball member 127 as described herein above. In an alternative, non-illustrated embodiment, spring 126 has a tapered configured and its proximal end engages with distal end 122 of spline member 120 instead of distal end 104 of elongated pin 102.

In one manner of assembling first arm member 30, engagement portion 46, spline member 120 and elongated pin 102 are first coupled together with cross pin 129. Spline member 113 and biasing member 109 are then placed over elongated pin 102 and elongated pin 102 is inserted into receptacle 94 until proximal end 103 engages with proximal end portion 96. Once proximal end 103 engages with proximal end portion 96, cross pin 108 can be inserted through bores 101 and 107 to couple elongated pin 102 with external housing 32. In this configuration, spring 110 becomes compressed between shoulder portion 96 of receptacle 94, which engages with proximal end 111 of spring 110, and proximal end 114 of spline member 113, which engages with distal end 112 of spring 110, thereby distally biasing spline member 113 into engagement with spline member 120. When spline member 113 is distally biased in this manner, hole 116 of spline member 113 is aligned with slot 100 extending through external housing 32 and release button 118 is engaged therewith. More particularly, release button 118 includes a stem 119 which extends through slot 100 and into engagement with hole 116. It should be appreciated that the engagement between release button 118 and spline member 113 prevents spline member 113 from rotating about elongated pin 102. In this configuration, spline member 113 serves as a locking element which limits the rotation of engagement portion 46 about elongated pin 102, further details of which will be provided below with respect to FIGS. 6-7. Moreover, release button 118 can be engaged by a user to compress spring 118 and disengage spline member 113 from spline member 120 to allow engagement portion 46 to rotate freely about elongated pin 102.

Figure 6:
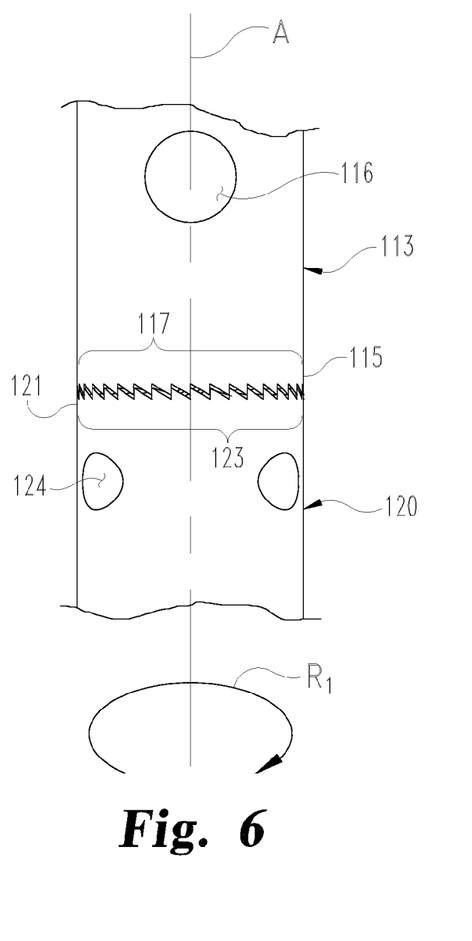
FIG. 6 is an enlarged plan view of corresponding spline members illustrated in FIG. 3 engaged with each other.

Referring generally to FIG. 6, an enlarged plan view of spline members 113, 120 is provided. While not illustrated, it should be appreciated that spline member 120 will generally be coupled with engagement portion 46 when it interacts with spline member 113. Accordingly, the rotational movements described with respect to spline member 120 will correspond to those of engagement portion 46 relative to external housing 32. Distal end 115 of spline member 113 includes a plurality of teeth 117 which are structured to interdigitate and engage with a plurality of teeth 123 positioned on proximal end 121 of spline member 120. As illustrated in FIG. 6, when teeth 117 and 123 engage with one another spline member 120 is allowed to rotate in a first direction but is prevented from rotating in an opposite, second direction. More particularly, teeth 123 of spline member 120 slip past teeth 117 of spline member 113 when spline member 120 is rotated in the direction indicated by directional arrow $R_1$, which corresponds to a clockwise direction, and spline member 120 is allowed to rotate freely in this direction relative to external housing 32. However, if a rotational force is applied to spline member 120 in the direction opposite of that indicated by directional arrow $R_1$, a counterclockwise direction, teeth 123 interlock with teeth 117 and prevent rotation of spline member 120 in such direction relative to external housing 32. Once spline member 113 is disengaged from spline member 120, spline member 120 is able to rotate freely about elongated pin 102.

Figure 7:
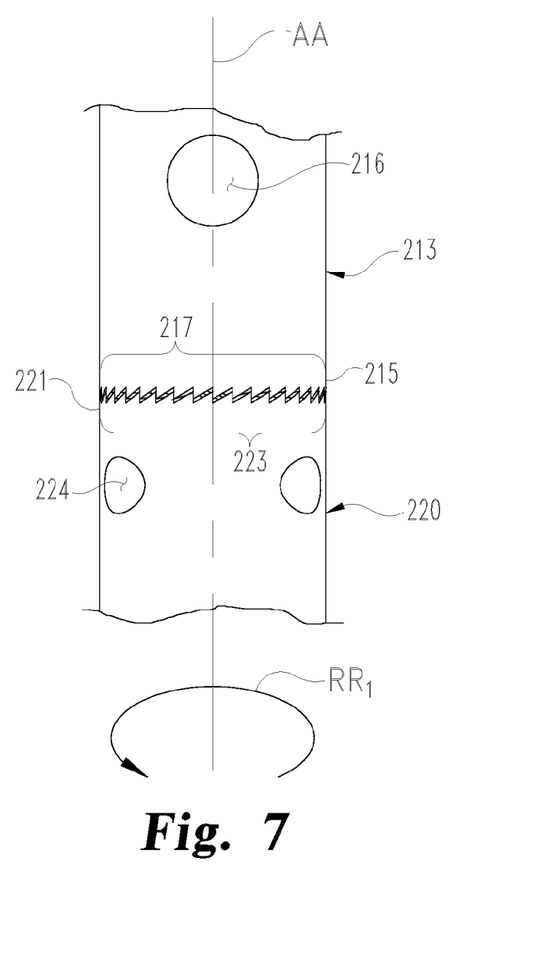
FIG. 7 is an enlarged plan view of alternative embodiment spline members engaged with each other.

Second arm member 130 includes spline members 213, 220 which are arranged differently from spline members 113, 120 described and illustrated with respect to first arm member 30. More particularly, with reference to FIG. 7, an enlarged plan view of spline members 213, 220 is provided. While not illustrated, it should be appreciated that spline member 220 will generally be engaged with engagement portion 146 when it interacts with spline member 213. Accordingly, the rotational movements described with respect to spline member 220 will correspond to those of engagement portion 146 relative to external housing 132. Distal end 215 of spline member 213 includes a plurality of teeth 217 which are structured to interdigitate and engage with a plurality of teeth 223 positioned on proximal end 221 of spline member 220. As illustrated in FIG. 7, when teeth 217 and 223 engage with one another, spline member 220 is allowed to rotate in a first direction but is prevented from rotating in an opposite, second direction. More particularly, teeth 223 of spline member 220 slip past teeth 217 of spline member 213 when spline member 220 is rotated in the direction indicated by directional arrow $RR_1$, which corresponds to a counter-clockwise direction, and spline member 220 is allowed to rotate freely in this direction relative to external housing 132. However, if a rotational force is applied to spline member 220 in the direction opposite of that indicated by directional arrow $RR_1$, a clockwise direction, teeth 223 interlock with teeth 217 and prevent rotation of spline member 220 in such direction relative to external housing 132. Once spline member 213 is disengaged from spline member 220, spline member 220 is able to rotate freely about elongated pin 202.

In view of the foregoing description, it should be appreciated that assembly 10 is configured such that first and second retractor blades 302, 342 can be pivoted or rotated toward one another about their first ends 304, 344 to provide working channel 390 with a tapered configuration that reduces in size from the second ends 306, 346 of retractor blades 302, 342 through the skin to the first ends 304, 344 of retractor blades 302, 342. More particularly, when engagement portion 46 is rotated clockwise and engagement portion 146 is rotated counter-clockwise, a separation distance between second ends 306, 346 of retractor blades 302, 342 is increased. Moreover, the engagement between teeth 113, 213 and teeth 123, 223 of spline members 113, 213 and 120, 220 allows a user to incrementally rotate engagement portions 46, 146 and increase the separation distance between second ends 306, 346 of retractor blades 302, 342. Additionally, unless release buttons 118, 218 are depressed by a user, the biasing of spline members 113, 213 into engagement with spline members 120, 220 prevents rotation of engagement portions 46, 146 in opposite directions and reduction of the separation distance between second ends 306, 346 of retractor blades 302, 342, thereby providing a desired configuration of working channel 390 for the duration of the surgical procedure. Among other things, a tapered working channel provides the surgeon greater access and increased visualization of the surgical site while minimizing tissue retraction. The tapered working channel 390 also allows greater angulation of instruments and implants placed through working channel 390, more selection in positioning of instruments and implants within working channel 390, and the ability to position instruments and implants adjacent the inner wall surfaces of the separated first and second retractor blades 302, 342, increasing the room available at the surgical site for multiple instruments and for orienting implants.

Figure 8:
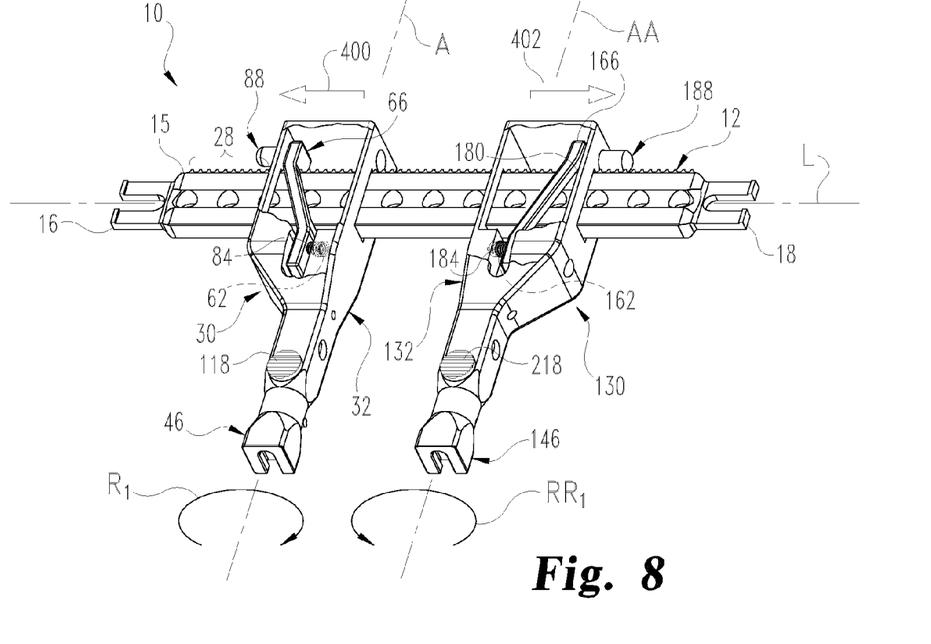
FIG. 8 is a perspective, partial cut-away view of the assembly of FIG. 1.
Figure 9:
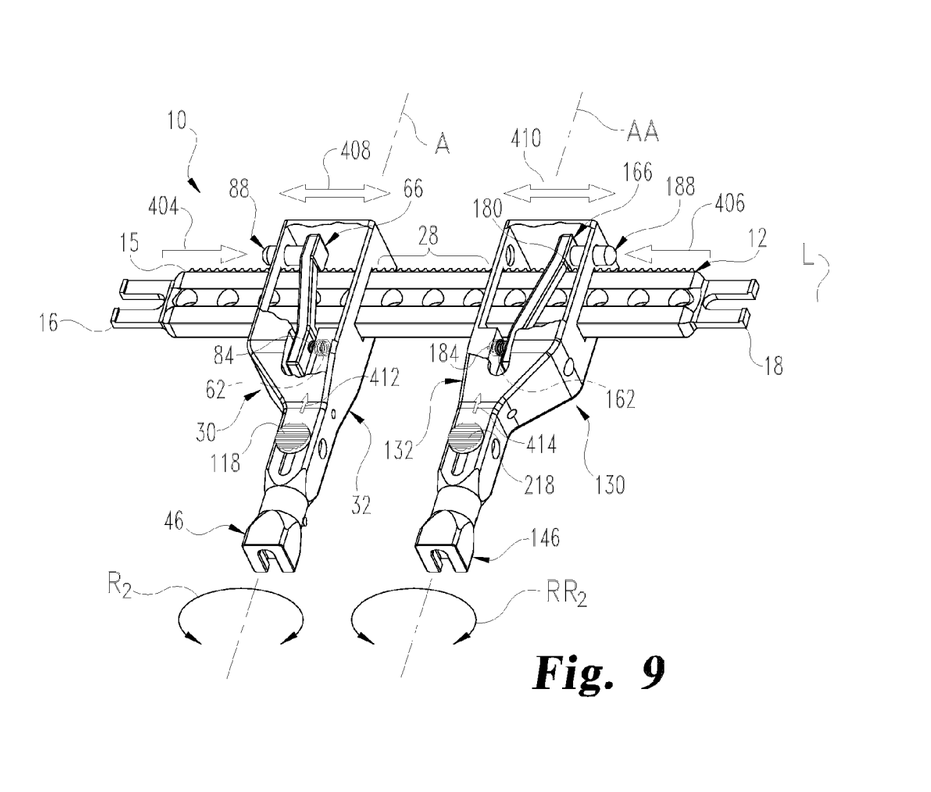
FIG. 9 is a perspective, partial cut-away view of the assembly of FIG. 1 illustrating various operating aspects of the assembly.

Further details regarding the operation of assembly 10 are now provided with respect to FIGS. 8 and 9. Springs 84, 184 engage with the distal end portions of locking members 66, 166 and bias the distal end portions of locking members 66, 166 toward first end 16 and second end 18, respectively, of elongate support member 12. Additionally, the proximal end portions of locking members 66, 166 are biased toward first end 16 and second end 18, respectively, of elongate support member 12, thereby advancing leading edges 80, 180 into engagement with teeth 28 on proximal surface 15 of elongate support member 12. As indicated above, when leading edges 80, 180 of locking members 66, 166 are engaged with proximal surface 15 of elongate support member 12, movement of first arm member 30 and second arm member 130 along elongate support member 12 is limited. More particularly, first arm member 30 is only movable toward first end 16 of elongate support member 12, as indicated by directional arrow 400, and second arm member 130 is only movable toward second end 18 of elongate support member 12, as indicated by directional arrow 402.

Movement of first arm member 30 and second arm member 130 away from one another as illustrated in FIG. 8 facilitates enlargement of working channel 390 between retractor portions 300, 340. Moreover, the engagement between arm members 30, 130 and elongate support member 12 allows a user to incrementally enlarge working channel 390 until a desired configuration is provided. Once a desired configuration of working channel 390 between retractor portions 300, 340 has been achieved, the engagement between leading edges 80, 180 and proximal surface 15 of elongate support member 12 retains working channel 390 in the desired configuration until the surgical procedure is complete. It should be appreciated that assembly 10 is operable to retain working channel 390 in the desired configuration without the use of additional instrumentation. However, the use of additional instrumentation to retain working channel 390 in the desired configuration is not precluded by the present application. Additionally, while not illustrated, it should be appreciated that arm members 30, 130 can be moved along elongate support member 12 by a health care professional to enlarge working channel 390. Alternatively, one or more separation instruments can be coupled to arm members 30, 130 or distractor portions 300, 340 to enlarge working channel 390. In one particular form, the separation instrument can be coupled between retractor portions 302, 342. Various non-limiting examples of separation instruments are provided in U.S.

Patent Publication No. 2004/0176665 to Branch et al., the contents of which were incorporated herein by reference in their entirety above.

With further regard to FIG. 8, release buttons 118, 218 have not been depressed and spline members 113, 213 remain engaged to spline members 120, 220. Accordingly, as discussed above, engagement portions 46, 146 are limited to rotation in the clockwise and counter-clockwise directions, as indicated by directional arrows $R_1$ and $RR_1$, respectively, and can be rotated to increase the separation distance between second ends 306, 346 of retractor blades 302, 342 and provide a tapered working channel 390. While not previously discussed, it should be appreciated that a user can engage one or both of engagement portions 46, 146 and retractor portions 300, 340 to facilitate rotation of engagement portions 46, 146 along axes A, AA, respectively. Alternatively, one or more instruments can be coupled to engagement portions 46, 146 or distractor portions 300, 340 to rotate engagement portions 46, 146 about axes A, AA.

Upon completion of the surgical procedure, arm members 30, 130 can be moved toward one another to reduce the size of working channel 390 to facilitate removal or repositioning of retractor portions 300, 340 at the surgical site. More particularly, as illustrated in FIG. 9, release buttons 88, 188 can be depressed as indicated by directional arrows 404, 406, respectively, thereby disengaging leading edges 80, 180 from engagement with proximal surface 15 of elongate support member 12 and allowing arm members 30, 130 to move freely along elongate support member 12 as indicated by directional arrows 408, 410, respectively. When release members 88, 188 are no longer depressed, leading edges 80, 180 are biased into engagement with proximal side 15 of elongate support member 12 and movement of arm members 30, 130 along elongate support member 12 is limited to the directions indicated by directional arrows 400, 402, respectively. As also illustrated in FIG. 9, release buttons 118, 218 can be moved proximally as indicated by directional arrows 412, 414, respectively, thereby facilitating rotation of engagement portions 46, 146 in clockwise and counter-clockwise directions about axes A, AA, as indicated by directional arrows $R_2$, $RR_2$. Accordingly, any tapered configuration of working channel 390 can be released to facilitate removal or repositioning of retractor portions 300, 340 at the surgical site, or the tapered configuration can be reconfigured.

In one embodiment, an assembly for percutaneous surgery in a patient includes an elongate support member extending between a first end and an opposite second end. The assembly also includes a first arm member positionable along the elongate support member. The first arm member includes an external housing extending between a proximal end including a passage sized and structured to receive the elongate support member and a distal end structured to engage with a first retractor portion. The external housing defines an internal chamber and the first arm member includes a first locking member positioned in the internal chamber. The assembly also includes a second arm member positionable along the elongate support member. The second arm member includes an external housing extending between a proximal end including a passage sized and structured to receive the elongate support member and a distal end structured to engage with a second retractor portion. The external housing defines an internal chamber and the second arm member includes a second locking member positioned in the internal chamber. Additionally, the elongate support member extends through an opening in each of the first and second locking members when the first and second arm members are positioned on the elongate support member. The first and second locking members are biased into engagement with the elongate support member, with the engagement between the first and second locking members and the elongate support member controlling movement of the first and second arm members along the elongate support member.

In another embodiment, an assembly for percutaneous surgery in a patient includes an elongate support member extending between a first end and an opposite second end. The assembly further includes a pair of arm members removably positioned on and movable along the elongate support member and engageable with a respective retractor portion. The arm members each include a passageway extending through an external housing and a locking member positioned in the external housing and the elongate support member extends through the passageway. Furthermore, the locking member of each of the arm members is releasably biased into engagement with the elongate support member. The engagement between the locking members and the elongate support member allows movement of the arm members along the elongate support member in opposite directions toward the first and second ends of the elongate support member and prevents movement of the arm members along the elongate support member toward one another.

In still another embodiment, an assembly for percutaneous surgery in a patient includes an elongate support member extending between a first end and an opposite second end. The assembly also includes a first arm member including an external housing extending along a longitudinal axis between a proximal end engageable with the elongate support member and an opposite distal end. The distal end includes a first engagement portion rotatably coupled to the first arm member and structured to engage with a first retractor portion. The assembly further includes a second arm member including an external housing extending along a longitudinal axis between a proximal end engageable with the elongate support member and an opposite distal end. The distal end includes a second engagement portion rotatably coupled to the second arm member and structured to engage with a second retractor portion. The external housing of each of the first and second arm members defines an elongated receptacle extending along the longitudinal axis from a distal opening at the distal end. The elongated receptacle includes a locking element releasably biased into engagement with a respective engagement portion. The engagement between the locking element and the respective engagement portion allows rotation of the engagement portion in a first direction about the longitudinal axis of a respective arm member and prevents rotational movement of the engagement portion in a second direction about the longitudinal axis of the respective arm member.

In still another embodiment, an assembly for percutaneous surgery in a patient includes an elongate support member extending between a first end and an opposite second end. The assembly also includes an arm member positionable along the elongate support member. The arm member includes an external housing extending between a proximal end including a passage sized and structured to receive the elongate support member and a distal end structured to engage with a retractor portion. The external housing defines an internal chamber and the arm member includes a locking member positioned in the internal chamber. Additionally, the elongate support member extends through an opening in the locking member when the arm member is positioned on the elongate support member. The locking member is biased into engagement with the elongate support member, with the engagement between the locking member and the elongate support member controlling movement of the arm member along the elongate support member.

In still another embodiment, an assembly for percutaneous surgery in a patient includes an elongate support member extending between a first end and an opposite second end. The assembly also includes an arm member including an external housing extending along a longitudinal axis between a proximal end engageable with the elongate support member and an opposite distal end. The distal end includes an engagement portion rotatably coupled to the arm member and structured to engage with a retractor portion. The external housing of the arm member defines an elongated receptacle extending along the longitudinal axis from a distal opening at the distal end. The elongated receptacle includes a locking element releasably biased into engagement with the engagement portion. The engagement between the locking element and the engagement portion allows rotation of the engagement portion in a first direction about the longitudinal axis of the arm member and prevents rotational movement of the engagement portion in a second direction about the longitudinal axis of the arm member.

Any theory, mechanism of operation, proof, or finding stated herein is meant to further enhance understanding of the present application and is not intended to make the present application in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the application, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the application as defined herein or by any of the following claims are desired to be protected.

What is claimed is:

1. An assembly for surgery in a patient, comprising:
an elongate support member extending between a first end and an opposite second end;
a first arm member positionable along said elongate support member, said first arm member including an external housing extending between a proximal end including a passage sized and structured to receive said elongate support member and a distal end structured to engage with a first retractor portion, said external housing defining an internal chamber and said first arm member including a first locking member positioned in said internal chamber and pivotably movable relative to said external housing;
a second arm member positionable along said elongate support member, said second arm member including an external housing extending between a proximal end including a passage sized and structured to receive said elongate support member and a distal end structured to engage with a second retractor portion, said external housing defining an internal chamber and said second arm member including a second locking member positioned in said internal chamber and pivotably movable relative to said external housing; and
wherein said elongate support member extends through an opening in each of said first and second locking members when said first and second arm members are positioned on said elongate support member, said first and second locking members being biased into engagement with said elongate support member and said engagement between said first and second locking members and said elongate support member limiting movement of said first and second arm members along said elongate support member,
wherein said external housing of each said first and second arm members defines a receptacle in said respective internal chamber, said first and second locking members each including a proximal end portion positioned adjacent to said proximal end of said external housing and a distal end portion positioned in said receptacle.

2. The assembly of claim 1, wherein said passage of each of said first and second arm members is defined by a pair of lateral openings through a sidewall of said external housing, said lateral openings of said first arm member being substantially aligned with said opening of said first locking member and said lateral openings of said second arm member being substantially aligned with said opening of said second locking member.

3. The assembly of claim 1, wherein said proximal end portion of said first and second locking members is laterally offset from said distal end portion of said first and second locking members.

4. The assembly of claim 1, wherein said receptacle is positioned between opposite lateral sidewalls of said external housing and said proximal end portion of said first and second locking members is positioned adjacent to one of said lateral sidewalls.

5. The assembly of claim 4, wherein each of said first and second arm members includes a bore extending transversely to and in communication with said receptacle, said bore including a compressible biasing member positioned between said distal end portion of said first and second locking members and an end wall of said bore.

6. The assembly of claim 1, wherein said elongate support member includes a plurality or teeth positioned along a proximal surface thereof, said plurality of teeth being engaged by a portion of an internal sidewall defining said opening of said respective first and second locking members; and said engagement between said first and second locking members and said elongate support member allows movement of said first and second arm members in opposite directions along said elongate support member toward said first and second ends of said elongate support member and prevents movement of said first and second arm members along said elongate support member toward one another.

7. An assembly for surgery in a patient, comprising:
an elongate support member extending between a first end and an opposite second end; a pair of arm members removably positioned on and movable along said elongate support member and engageable with a respective retractor portion, said arm members each including a passageway extending through an external housing and a locking member positioned in said external housing, said elongate support member extending through said passageway, each of said arm members includes a compressible biasing member positioned in an internal bore against said distal end portion of said locking member; and wherein said locking member of each of said arm members is releasably biased into engagement with said elongate support member, said engagement between said locking members and said elongate support member allowing movement of said arm members along said elongate support member in opposite directions toward said first and second ends of said elongate support member and preventing movement of said arm members along said elongate support member toward one another, wherein said passageway of each of said arm members is defined by a pair of oppositely positioned passages extending through lateral sidewalls of said external housing and an opening in art intermediate portion of said locking member, said intermediate portion extending between a proximal end portion and a distal end portion laterally offset from said proximal end portion, wherein each of said arm members includes a projection extending through a first one of said lateral sidewalls of said external housing, said projection communicating with said locking member and being movable relative to said external housing to facilitate disengagement of said locking member from said elongate support member, said disengagement facilitating bidirectional movement of said arm members along said elongate support member.

8. The assembly of claim 7, wherein said external housing of each of said arm members extends along a longitudinal axis between a proximal end positioned adjacent to said elongate support member and a distal end including an engagement portion structured to engage with the respective retractor portion.

9. The assembly of claim 8, wherein said external housing of each of said arm members defines an elongated receptacle extending along said longitudinal axis from said distal end toward said proximal end, said elongated receptacle including a locking element releasably biased into engagement with said engagement portion, said engagement between said locking element and said engagement portion allowing rotational movement of said engagement portion in a first direction about the longitudinal axis of said respective arm member and preventing rotational movement of said engagement portion in a second direction about the longitudinal axis of said respective arm member.

10. The assembly of claim 9, further comprising a first retractor portion engaged with said engagement portion of a first one of said arm members and a second retractor portion engaged with said engagement portion of a second one of said arm members, said first and second retractor portions each including a first end and an opposite second end positionable in an incision.

11. An assembly for surgery in a patent, comprising:
an elongate support member extending between a first end and an opposite second end;
a first aril member including an external housing extending along a longitudinal axis between a proximal end engageable with said elongate support member and an opposite distal end, said distal end including a first engagement portion rotatably coupled to said first arm member and structured to engage with a first retractor portion and rotate said first retractor portion about an axis A 360 degrees;
a second arm member including an external housing extending along a longitudinal axis between a proximal end engageable with said elongate support member and an opposite distal end, said distal and including a second engagement portion rotatably coupled to said second arm member and structured to engage with a second retractor portion and rotate said second retractor portion about an axis AA 360 degrees, said first and second arm members each include an elongated cylindrical member extending distally of said distal opening from a proximal portion of said elongated receptacle; and said first and second engagement portions each define an internal recess receiving a distal end of a respective elongated cylindrical member; and wherein said external housing of each of said first and second arm members defines an elongated receptacle extending along said longitudinal axis from a distal opening at said distal end, said elongated receptacle including a locking element axially movable along said longitudinal axis and releasably biased into engagement with a respective engagement portion, said engagement between said locking element and said respective engagement portion allowing rotation of said engagement portion in a first direction about the longitudinal axis of a respective arm member and preventing rotational movement of said engagement portion in a second direction about the longitudinal axis of said respective arm member, wherein said elongated receptacle of each of first and second arm members includes a compressible biasing member positioned about said elongated cylindrical member between an enlarged shoulder portion of said elongated receptacle and said locking element; said locking element, of each of said first and second arm members is positioned about said elongated cylindrical member between said biasing member and a respective engagement portion and said locking element includes a distal end with a splined configuration structured to engage with a corresponding splined configuration on a proximal end of said respective engagement portion.

12. The assembly of claim 11, further comprising: a first retractor portion including a first end engaged with said first engagement portion and a second end positionable in an incision; a second retractor portion including a first end engaged with sad second engagement portion and a second end positionable in the incision opposite said second end of said first retractor portion; and wherein rotation of said first and second engagement portions about said longitudinal axes of said first and second arm members in said first direction increases a separation distance between said second ends of said first and second retractor portions.

13. The assembly of claim 12, wherein said first direction is clockwise for said first engagement portion and counter-clockwise for said second engagement portion and said second direction is counter-clockwise for said first engagement portion and clockwise for said second engagement portion.

14. The assembly of claim 11, wherein each of said first and second arm members includes a release button extending from said locking element through an elongated slot in said external housing, said release button restricting rotation of said locking element about said elongated cylindrical member and being movable relative to said external housing to compress said biasing member and facilitate disengagement of said locking element from a respective engagement portion, said disengagement allowing rotational movement at said respective engagement portion about said longitudinal axis in said first and second directions.

* * * * *